(12) United States Patent
Ruchti et al.

(10) Patent No.: US 10,042,986 B2
(45) Date of Patent: Aug. 7, 2018

(54) INFUSION PUMP AUTOMATION SYSTEM AND METHOD

(71) Applicant: ICU Medical, Inc., San Clemente, CA (US)

(72) Inventors: Timothy L. Ruchti, Gurnee, IL (US); Harsh Dharwad, San Diego, CA (US); Lynn D. Neuhardt, Lakeside, CA (US); Aaron P. Perez, Murrieta, CA (US)

(73) Assignee: ICU Medical, Inc., San Clemente, CA (US)

( * ) Notice: Subject to any disclaimer, the term of this patent is extended or adjusted under 35 U.S.C. 154(b) by 115 days.

(21) Appl. No.: 14/547,376

(22) Filed: Nov. 19, 2014

(65) Prior Publication Data
US 2015/0141955 A1 May 21, 2015

Related U.S. Application Data

(60) Provisional application No. 61/906,181, filed on Nov. 19, 2013.

(51) Int. Cl.
*A61M 5/142* (2006.01)
*G06F 19/00* (2018.01)

(52) U.S. Cl.
CPC ......... *G06F 19/3468* (2013.01); *A61M 5/142* (2013.01); *A61M 2005/14208* (2013.01); *A61M 2205/502* (2013.01)

(58) Field of Classification Search
CPC ... A61M 2005/14208; A61M 2205/502; G06F 19/3468
(Continued)

(56) References Cited

U.S. PATENT DOCUMENTS 4,024,864 A   5/1977   Davies et al.
4,055,175 A   10/1977  Clemens et al.
(Continued)

FOREIGN PATENT DOCUMENTS

CA   2 060 151   8/1997
CA   2 125 300   10/1999
(Continued)

OTHER PUBLICATIONS

PCT/US2014066379, Notification of Transmittal of the International Search Report and Written Opinion of the International Searching Authority, dated Feb. 2, 2015, 11 pages.
(Continued)

*Primary Examiner* — Kevin C Sirmons
*Assistant Examiner* — Deanna K Hall
(74) *Attorney, Agent, or Firm* — Knobbe, Martens, Olson & Bear, LLP

(57) ABSTRACT

An infusion pump automation system and method includes a remote processor and an infusion pump having an infusion pump user interface, including a touch screen display, and associated infusion pump infusion state and infusion pump user interface state. The remote processor is remote to the infusion pump and includes a controller interface and a controller, such that the controller bidirectionally communicates with the infusion pump, determines a current infusion state of the infusion pump and a current infusion pump user interface state and accepts a command to remotely change the infusion state of the infusion pump from an external server. The controller determines if the command is consistent with the current infusion state of the infusion pump and the current infusion pump user interface state, executes the command if the command is able to be successfully executed, and confirms that the command is successfully executed.

7 Claims, 4 Drawing Sheets

(58) Field of Classification Search
USPC .................................................. 604/67, 151
See application file for complete search history.

(56) References Cited

U.S. PATENT DOCUMENTS

| | | | |
|---|---|---|---|
| 4,151,845 A | 5/1979 | Clemens |
| 4,213,454 A | 7/1980 | Shim |
| 4,240,438 A | 12/1980 | Updike et al. |
| 4,280,494 A | 7/1981 | Cosgrove et al. |
| 4,308,866 A | 1/1982 | Jeliffe |
| 4,370,983 A | 2/1983 | Lichtenstein et al. |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,494,950 A | 1/1985 | Fischell |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,551,133 A | 11/1985 | Zegers de Beyl et al. |
| 4,553,958 A | 11/1985 | LeCocq |
| 4,559,037 A | 12/1985 | Franetzki et al. |
| 4,613,937 A | 9/1986 | Batty |
| 4,624,661 A | 11/1986 | Arimond |
| 4,633,878 A | 1/1987 | Bombardieri |
| 4,634,426 A | 1/1987 | Kamen |
| 4,634,427 A | 1/1987 | Hannula et al. |
| 4,674,652 A | 6/1987 | Aten et al. |
| 4,676,776 A | 6/1987 | Howson et al. |
| 4,679,562 A | 7/1987 | Luksha |
| 4,685,903 A | 8/1987 | Cable et al. |
| 4,695,954 A | 9/1987 | Rose |
| 4,696,671 A | 9/1987 | Epstein et al. |
| 4,714,462 A | 12/1987 | DiDomenico |
| 4,722,734 A | 2/1988 | Kolin |
| 4,731,051 A | 3/1988 | Fischell |
| 4,741,732 A | 5/1988 | Crankshaw et al. |
| 4,756,706 A | 7/1988 | Kerns et al. |
| 4,776,842 A | 10/1988 | Franetzki et al. |
| 4,785,969 A | 11/1988 | McLaughlin |
| 4,803,625 A | 2/1989 | Fu et al. |
| 4,835,372 A | 5/1989 | Gombrich et al. |
| 4,838,275 A | 6/1989 | Lee |
| 4,838,856 A | 6/1989 | Mulreany et al. |
| 4,838,857 A | 6/1989 | Strowe et al. |
| 4,854,324 A | 8/1989 | Hirschman et al. |
| 4,857,716 A | 8/1989 | Gombrich et al. |
| 4,858,154 A | 8/1989 | Anderson et al. |
| 4,898,578 A | 2/1990 | Rubalcaba, Jr. |
| 4,908,017 A | 3/1990 | Howson et al. |
| 4,933,873 A | 6/1990 | Kaufman et al. |
| 4,943,279 A | 7/1990 | Samiotes et al. |
| 4,946,439 A | 8/1990 | Eggers |
| 4,953,745 A | 9/1990 | Rowlett |
| 4,978,335 A | 12/1990 | Arthur, III |
| 5,000,739 A | 3/1991 | Kulisz et al. |
| 5,010,473 A | 4/1991 | Jacobs |
| 5,014,698 A | 5/1991 | Cohen |
| 5,016,172 A | 5/1991 | Dessertine |
| 5,026,084 A | 6/1991 | Paisfield |
| 5,034,004 A | 7/1991 | Crankshaw |
| 5,041,086 A | 8/1991 | Koenig et al. |
| 5,058,161 A | 10/1991 | Weiss |
| 5,078,683 A | 1/1992 | Sancoff et al. |
| 5,084,828 A | 1/1992 | Kaufman et al. |
| 5,088,981 A | 2/1992 | Howson et al. |
| 5,097,505 A | 3/1992 | Weiss |
| 5,100,380 A | 3/1992 | Epstein et al. |
| 5,102,392 A | 4/1992 | Sakai et al. |
| 5,104,374 A | 4/1992 | Bishko et al. |
| 5,109,850 A | 5/1992 | Blanco et al. |
| 5,131,816 A | 7/1992 | Brown |
| 5,142,484 A | 8/1992 | Kaufman et al. |
| 5,153,827 A | 10/1992 | Coutre et al. |
| 5,157,640 A | 10/1992 | Backner |
| 5,161,222 A | 11/1992 | Montejo et al. |
| 5,177,993 A | 1/1993 | Beckman et al. |
| 5,181,910 A | 1/1993 | Scanlon |
| 5,190,522 A | 3/1993 | Wocicki et al. |
| 5,199,439 A | 4/1993 | Zimmerman et al. |
| 5,200,891 A | 4/1993 | Kehr et al. |
| 5,216,597 A | 6/1993 | Beckers |
| 5,221,268 A | 6/1993 | Barton et al. |
| 5,230,061 A | 7/1993 | Welch |
| 5,243,982 A | 9/1993 | Möstl et al. |
| 5,244,463 A | 9/1993 | Cordner, Jr. et al. |
| 5,249,260 A | 9/1993 | Nigawara et al. |
| 5,256,156 A | 10/1993 | Kern et al. |
| 5,256,157 A | 10/1993 | Samiotes et al. |
| 5,261,702 A | 11/1993 | Mayfield |
| 5,317,506 A | 5/1994 | Coutre et al. |
| 5,319,355 A | 6/1994 | Russek |
| 5,319,363 A | 6/1994 | Welch et al. |
| 5,330,634 A | 7/1994 | Wong et al. |
| 5,338,157 A | 8/1994 | Blomquist |
| 5,341,476 A | 8/1994 | Lowell |
| 5,364,346 A | 11/1994 | Schrezenmeir |
| 5,366,346 A | 11/1994 | Danby |
| 5,368,562 A | 11/1994 | Blomquist et al. |
| 5,373,454 A | 12/1994 | Kanda et al. |
| 5,376,070 A | 12/1994 | Purvis et al. |
| 5,378,231 A | 1/1995 | Johnson et al. |
| 5,389,071 A | 2/1995 | Kawahara et al. |
| 5,389,078 A | 2/1995 | Zalesky et al. |
| 5,417,222 A | 5/1995 | Dempsey et al. |
| 5,423,748 A | 6/1995 | Uhala |
| 5,429,602 A | 7/1995 | Hauser |
| 5,431,627 A | 7/1995 | Pastrone et al. |
| 5,432,777 A | 7/1995 | Le Boudec et al. |
| 5,445,621 A | 8/1995 | Poli et al. |
| 5,447,164 A | 9/1995 | Shaya et al. |
| 5,455,851 A | 10/1995 | Chaco et al. |
| 5,461,365 A | 10/1995 | Schlager et al. |
| 5,464,392 A | 11/1995 | Epstein et al. |
| 5,465,082 A | 11/1995 | Chaco |
| 5,485,408 A | 1/1996 | Blomquist |
| 5,493,430 A | 2/1996 | Lu et al. |
| 5,496,273 A | 3/1996 | Pastrone et al. |
| 5,505,828 A | 4/1996 | Wong et al. |
| 5,507,288 A | 4/1996 | Bocker et al. |
| 5,507,786 A | 4/1996 | Morgan et al. |
| 5,508,499 A | 4/1996 | Ferrario |
| 5,515,713 A | 5/1996 | Saugues et al. |
| 5,520,637 A | 5/1996 | Pager et al. |
| 5,522,798 A | 6/1996 | Johnson et al. |
| 5,547,470 A | 8/1996 | Johnson et al. |
| 5,554,013 A | 9/1996 | Owens et al. |
| 5,562,615 A | 10/1996 | Nassif |
| 5,577,169 A | 11/1996 | Prezioso |
| 5,582,323 A | 12/1996 | Kurtenbach |
| 5,582,593 A | 12/1996 | Hultman |
| 5,594,786 A | 1/1997 | Chaco et al. |
| 5,598,519 A | 1/1997 | Narayanan |
| 5,620,608 A | 4/1997 | Rosa et al. |
| 5,630,710 A | 5/1997 | Tune et al. |
| 5,636,044 A | 6/1997 | Yuan et al. |
| 5,643,212 A | 7/1997 | Coutre et al. |
| 5,651,775 A | 7/1997 | Walker et al. |
| 5,658,131 A | 8/1997 | Aoki et al. |
| 5,658,250 A | 8/1997 | Blomquist et al. |
| 5,665,065 A | 9/1997 | Colman et al. |
| 5,669,877 A | 9/1997 | Blomquist |
| 5,672,154 A | 9/1997 | Sillén et al. |
| 5,681,285 A | 10/1997 | Ford et al. |
| 5,685,844 A | 11/1997 | Marttila |
| 5,687,717 A | 11/1997 | Halpern et al. |
| 5,689,229 A | 11/1997 | Chaco et al. |
| 5,697,899 A | 12/1997 | Hillman et al. |
| 5,699,509 A | 12/1997 | Gary et al. |

(56) References Cited

U.S. PATENT DOCUMENTS

| | | | |
|---|---|---|---|
| 5,713,856 A | 2/1998 | Eggers et al. | |
| 5,718,562 A | 2/1998 | Lawless et al. | |
| 5,719,761 A | 2/1998 | Gatti et al. | |
| 5,733,259 A | 3/1998 | Valcke et al. | |
| 5,738,102 A | 4/1998 | Lemelson | |
| 5,744,027 A | 4/1998 | Connell et al. | |
| 5,752,621 A | 5/1998 | Passamante | |
| 5,754,111 A | 5/1998 | Garcia | |
| 5,764,034 A | 6/1998 | Bowman et al. | |
| 5,764,159 A | 6/1998 | Neftel et al. | |
| 5,772,635 A | 6/1998 | Dastur et al. | |
| 5,774,865 A | 6/1998 | Glynn | |
| 5,778,256 A | 7/1998 | Darbee | |
| 5,778,345 A | 7/1998 | McCartney | |
| 5,781,442 A | 7/1998 | Engleson et al. | |
| 5,782,805 A | 7/1998 | Meinzer et al. | |
| 5,788,669 A | 8/1998 | Peterson | |
| 5,797,515 A | 8/1998 | Liff et al. | |
| 5,800,387 A | 9/1998 | Duffy et al. | |
| 5,814,015 A * | 9/1998 | Gargano | A61M 5/1456 604/151 |
| 5,822,544 A | 10/1998 | Chaco et al. | |
| 5,822,715 A | 10/1998 | Worthington et al. | |
| 5,827,179 A | 10/1998 | Lichter et al. | |
| 5,832,448 A | 11/1998 | Brown | |
| 5,836,910 A | 11/1998 | Duffy et al. | |
| 5,850,344 A | 12/1998 | Conkright | |
| 5,867,821 A | 2/1999 | Ballantyne et al. | |
| 5,870,733 A | 2/1999 | Bass et al. | |
| 5,871,465 A | 2/1999 | Vasko | |
| 5,873,731 A | 2/1999 | Predergast | |
| 5,885,245 A | 3/1999 | Lynch et al. | |
| 5,897,493 A | 4/1999 | Brown | |
| 5,897,498 A | 4/1999 | Canfield, II et al. | |
| 5,910,252 A | 6/1999 | Truitt et al. | |
| 5,912,818 A | 6/1999 | McGrady et al. | |
| 5,915,240 A | 6/1999 | Karpf | |
| 5,920,054 A | 7/1999 | Uber, III | |
| 5,920,263 A | 7/1999 | Huttenhoff et al. | |
| 5,924,074 A | 7/1999 | Evans | |
| 5,931,764 A | 8/1999 | Freeman et al. | |
| 5,935,099 A | 8/1999 | Peterson et al. | |
| 5,935,106 A | 8/1999 | Olsen | |
| 5,941,846 A | 8/1999 | Duffy et al. | |
| 5,956,501 A | 9/1999 | Brown | |
| 5,957,885 A | 9/1999 | Bollish et al. | |
| 5,960,085 A | 9/1999 | de la Huerga | |
| 5,961,448 A | 10/1999 | Swenson et al. | |
| 5,967,559 A | 10/1999 | Abramowitz | |
| 5,971,594 A | 10/1999 | Sahai et al. | |
| 5,975,081 A | 11/1999 | Hood et al. | |
| 5,990,838 A | 11/1999 | Burns et al. | |
| 5,997,476 A | 12/1999 | Brown | |
| 6,000,828 A | 12/1999 | Leet | |
| 6,003,006 A | 12/1999 | Colella et al. | |
| 6,012,034 A | 1/2000 | Hamparian et al. | |
| 6,017,318 A | 1/2000 | Gauthier et al. | |
| 6,021,392 A | 2/2000 | Lester et al. | |
| 6,024,539 A | 2/2000 | Blomquist | |
| 6,032,155 A | 2/2000 | de la Huerga | |
| 6,032,676 A | 3/2000 | Moore | |
| 6,073,106 A | 6/2000 | Rozen et al. | |
| 6,104,295 A | 8/2000 | Gaisser et al. | |
| 6,112,182 A | 8/2000 | Akers et al. | |
| RE36,871 E | 9/2000 | Epstein et al. | |
| 6,115,390 A | 9/2000 | Chuah | |
| 6,122,536 A | 9/2000 | Sun et al. | |
| 6,126,637 A | 10/2000 | Kriesel et al. | |
| 6,135,949 A | 10/2000 | Russo et al. | |
| 6,150,942 A | 11/2000 | O'Brien | |
| 6,151,643 A | 11/2000 | Cheng et al. | |
| 6,157,914 A | 12/2000 | Seto et al. | |
| 6,159,147 A | 12/2000 | Lichter et al. | |
| 6,167,567 A | 12/2000 | Chiles et al. | |
| 6,182,667 B1 | 2/2001 | Hanks et al. | |
| 6,189,105 B1 | 2/2001 | Lopes | |
| 6,195,589 B1 | 2/2001 | Ketcham | |
| 6,208,974 B1 | 3/2001 | Campbell et al. | |
| 6,222,323 B1 | 4/2001 | Yamashita et al. | |
| 6,223,440 B1 | 5/2001 | Rashman | |
| 6,226,277 B1 | 5/2001 | Chuah | |
| 6,227,371 B1 | 5/2001 | Song | |
| 6,234,176 B1 | 5/2001 | Domae et al. | |
| 6,241,704 B1 | 6/2001 | Peterson et al. | |
| 6,248,067 B1 | 6/2001 | Causey, III et al. | |
| 6,249,705 B1 | 6/2001 | Snell | |
| 6,257,265 B1 | 7/2001 | Brunner et al. | |
| 6,259,355 B1 | 7/2001 | Chaco et al. | |
| 6,269,340 B1 | 7/2001 | Ford et al. | |
| 6,270,455 B1 | 8/2001 | Brown | |
| 6,271,813 B1 | 8/2001 | Palalau | |
| 6,277,072 B1 | 8/2001 | Bardy | |
| 6,280,380 B1 | 8/2001 | Bardy | |
| 6,283,761 B1 | 9/2001 | Joao | |
| 6,285,665 B1 | 9/2001 | Chuah | |
| 6,292,860 B1 | 9/2001 | Cochcroft, Jr. | |
| 6,312,378 B1 | 11/2001 | Bardy | |
| 6,327,254 B1 | 12/2001 | Chuah | |
| 6,330,008 B1 | 12/2001 | Razdow et al. | |
| 6,339,718 B1 | 1/2002 | Zatezalo et al. | |
| 6,346,886 B1 | 2/2002 | de la Huerga | |
| 6,363,282 B1 | 3/2002 | Nichols et al. | |
| 6,371,719 B1 | 4/2002 | Hildebrandt | |
| 6,377,548 B1 | 4/2002 | Chuah | |
| 6,388,951 B1 | 5/2002 | Matsumoto et al. | |
| 6,406,426 B1 | 6/2002 | Reuss et al. | |
| 6,408,330 B1 | 6/2002 | de la Huerga | |
| 6,418,334 B1 | 7/2002 | Unger et al. | |
| 6,427,088 B1 | 7/2002 | Bowman et al. | |
| 6,428,483 B1 | 8/2002 | Carlebach | |
| 6,442,432 B2 | 8/2002 | Lee | |
| 6,469,991 B1 | 10/2002 | Chuah | |
| 6,475,180 B2 | 11/2002 | Peterson et al. | |
| 6,482,158 B2 | 11/2002 | Mault | |
| 6,485,418 B2 | 11/2002 | Yasushi et al. | |
| 6,494,694 B2 | 12/2002 | Lawless et al. | |
| 6,494,831 B1 | 12/2002 | Koritzinsky | |
| 6,497,680 B1 | 12/2002 | Hoist et al. | |
| 6,514,460 B1 | 2/2003 | Fendrock | |
| 6,517,482 B1 | 2/2003 | Eiden et al. | |
| 6,519,569 B1 | 2/2003 | White et al. | |
| 6,520,930 B2 | 2/2003 | Critchlow et al. | |
| 6,540,672 B1 | 4/2003 | Simonsen et al. | |
| 6,542,902 B2 | 4/2003 | Dulong et al. | |
| 6,544,212 B2 | 4/2003 | Galley et al. | |
| 6,544,228 B1 | 4/2003 | Heitmeier | |
| 6,546,350 B1 | 4/2003 | Hartmann et al. | |
| 6,551,276 B1 | 4/2003 | Mann et al. | |
| 6,554,798 B1 | 4/2003 | Mann et al. | |
| 6,558,320 B1 | 5/2003 | Causey et al. | |
| 6,558,351 B1 | 5/2003 | Steil et al. | |
| 6,565,509 B1 | 5/2003 | Say et al. | |
| 6,567,416 B1 | 5/2003 | Chuah | |
| 6,571,294 B2 | 5/2003 | Simmon et al. | |
| 6,572,542 B1 | 6/2003 | Houben et al. | |
| 6,572,545 B2 | 6/2003 | Knobbe et al. | |
| 6,578,002 B1 | 6/2003 | Derzay et al. | |
| 6,581,117 B1 | 6/2003 | Klein et al. | |
| 6,587,034 B1 | 7/2003 | Heiman et al. | |
| 6,589,229 B1 | 7/2003 | Connelly et al. | |
| 6,599,281 B1 | 7/2003 | Struys et al. | |
| 6,602,191 B2 | 8/2003 | Ouy | |
| 6,605,072 B2 | 8/2003 | Struys et al. | |
| 6,628,809 B1 | 9/2003 | Rowe et al. | |
| 6,631,353 B1 | 10/2003 | Davis et al. | |
| 6,640,246 B1 | 10/2003 | Gardy, Jr. et al. | |
| 6,641,533 B2 | 11/2003 | Causey, III et al. | |
| 6,647,299 B2 | 11/2003 | Bourget | |
| 6,652,455 B1 | 11/2003 | Kocher | |
| 6,653,937 B2 | 11/2003 | Nelson et al. | |
| 6,659,947 B1 | 12/2003 | Carter et al. | |
| 6,669,630 B1 | 12/2003 | Joliat et al. | |
| 6,671,563 B1 | 12/2003 | Engleson et al. | |
| 6,673,033 B1 | 1/2004 | Sciulli et al. | |

(56) References Cited

U.S. PATENT DOCUMENTS

| | | |
|---|---|---|
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Cmkovich et al. |
| 6,780,156 B2 | 8/2004 | Haueter et al. |
| 6,790,198 B1 | 9/2004 | White et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,936,029 B2 | 8/2005 | Mann et al. |
| 6,945,954 B2 | 9/2005 | Hochman et al. |
| 6,948,492 B2 | 9/2005 | Wemeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 | 8/2007 | Staehr et al. |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |
| 7,343,224 B2 | 3/2008 | DiGianfilippo et al. |
| 7,346,025 B2 | 3/2008 | Bryson |
| 7,347,836 B2 | 3/2008 | Peterson et al. |
| 7,354,420 B2 | 4/2008 | Steil et al. |
| 7,369,897 B2 | 5/2008 | Boveja et al. |
| 7,369,948 B1 | 5/2008 | Ferenczi et al. |
| 7,383,088 B2 | 6/2008 | Spinelli et al. |
| 7,384,410 B2 | 6/2008 | Eggers et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,420,472 B2 | 9/2008 | Tran |
| 7,454,314 B2 | 11/2008 | Holland et al. |
| 7,457,804 B2 | 11/2008 | Uber, III et al. |
| 7,464,040 B2 | 12/2008 | Joao |
| 7,471,994 B2 | 12/2008 | Ford et al. |
| 7,483,756 B2 | 1/2009 | Engleson et al. |
| 7,489,808 B2 | 2/2009 | Gerder |
| 7,490,021 B2 | 2/2009 | Holland et al. |
| 7,490,048 B2 | 2/2009 | Joao |
| 7,491,187 B2 | 2/2009 | Van Den Berghe et al. |
| 7,524,304 B2 | 4/2009 | Genosar |
| 7,551,078 B2 | 6/2009 | Carlson |
| 7,559,321 B2 | 7/2009 | Wermeling et al. |
| 7,565,197 B2 | 7/2009 | Haulbrich et al. |
| 7,572,230 B2 | 8/2009 | Neumann et al. |
| 7,578,802 B2 | 8/2009 | Hickle |
| 7,621,009 B2 | 11/2009 | Elhabashy |
| D606,533 S | 12/2009 | De Jong et al. |
| 7,636,718 B1 | 12/2009 | Steen et al. |
| 7,640,172 B2 | 12/2009 | Kuth |
| 7,645,258 B2 | 1/2010 | White et al. |
| 7,647,237 B2 | 1/2010 | Malave et al. |
| 7,662,124 B2 | 2/2010 | Duchon et al. |
| 7,668,731 B2 | 2/2010 | Martucci et al. |
| 7,671,733 B2 | 3/2010 | McNeal |

(56) References Cited

U.S. PATENT DOCUMENTS

| | | |
|---|---|---|
| 7,678,071 B2 | 3/2010 | Lebel et al. |
| 7,687,678 B2 | 3/2010 | Jacobs |
| 7,697,994 B2 | 4/2010 | VanDanacker et al. |
| 7,698,239 B2 | 4/2010 | Lieuallen |
| 7,724,147 B2 | 5/2010 | Brown et al. |
| 7,739,126 B1 | 6/2010 | Cave |
| 7,746,218 B2 | 6/2010 | Collins, Jr. |
| 7,766,873 B2 | 8/2010 | Moberg et al. |
| 7,776,029 B2 | 8/2010 | Whitehurst et al. |
| 7,776,031 B2 | 8/2010 | Hartlaub et al. |
| 7,785,313 B2 | 8/2010 | Mastrototaro |
| 7,806,852 B1 | 10/2010 | Jurson |
| 7,806,886 B2 | 10/2010 | Kanderian, Jr. et al. |
| 7,826,981 B2 | 11/2010 | Goode, Jr. et al. |
| 7,835,927 B2 | 11/2010 | Schlotterbeck et al. |
| 7,836,314 B2 | 11/2010 | Chieu |
| 7,856,276 B2 | 12/2010 | Ripart et al. |
| 7,860,583 B2 | 12/2010 | Condurso et al. |
| 7,871,394 B2 | 1/2011 | Halbert et al. |
| 7,886,231 B2 | 2/2011 | Hopermann et al. |
| 7,895,053 B2 | 2/2011 | Holland et al. |
| 7,899,546 B2 | 3/2011 | Sieracki et al. |
| 7,905,710 B2 | 3/2011 | Wang et al. |
| 7,920,061 B2 | 4/2011 | Klein et al. |
| 7,933,780 B2 | 4/2011 | de la Huerga |
| 7,938,796 B2 | 5/2011 | Moubayed |
| 7,974,714 B2 | 7/2011 | Hoffberg |
| 7,996,241 B2 | 8/2011 | Zak |
| 8,034,026 B2 | 10/2011 | Grant |
| 8,038,593 B2 | 10/2011 | Friedman et al. |
| 8,048,040 B2 | 11/2011 | Kiani |
| 8,060,576 B2 | 11/2011 | Chan et al. |
| 8,065,161 B2 | 11/2011 | Howard et al. |
| 8,066,672 B2 | 11/2011 | Mandro |
| 8,078,983 B2 | 12/2011 | Davis et al. |
| 8,082,018 B2 | 12/2011 | Duchon et al. |
| 8,082,312 B2 | 12/2011 | Chan et al. |
| 8,147,448 B2 | 4/2012 | Sundar et al. |
| 8,149,131 B2 | 4/2012 | Blornquist |
| 8,169,914 B2 | 5/2012 | Bajpai |
| 8,171,094 B2 | 5/2012 | Chan et al. |
| 8,185,322 B2 | 5/2012 | Schroeder et al. |
| 8,195,478 B2 | 6/2012 | Petersen et al. |
| 8,206,350 B2 | 6/2012 | Mann et al. |
| 8,219,413 B2 | 7/2012 | Martinez et al. |
| 8,234,128 B2 | 7/2012 | Martucci et al. |
| 8,267,892 B2 | 9/2012 | Spencer et al. |
| 8,271,106 B2 | 9/2012 | Wehba et al. |
| 8,287,495 B2 | 10/2012 | Michaud et al. |
| 8,291,337 B2 | 10/2012 | Gannin et al. |
| 8,298,184 B2 | 10/2012 | DiPerna et al. |
| 8,352,290 B2 | 1/2013 | Bartz et al. |
| 8,359,338 B2 | 1/2013 | Butterfield et al. |
| 8,380,536 B2 | 2/2013 | Howard et al. |
| 8,387,112 B1 | 2/2013 | Ranjan et al. |
| 8,394,077 B2 | 3/2013 | Jacobson et al. |
| 8,403,908 B2 | 3/2013 | Jacobson et al. |
| 8,435,206 B2 | 5/2013 | Evans et al. |
| 8,449,523 B2 | 5/2013 | Brukalo et al. |
| 8,452,953 B2 | 5/2013 | Buck et al. |
| 8,453,645 B2 | 6/2013 | Figueiredo et al. |
| 8,480,648 B2 | 7/2013 | Burnett et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,543,416 B2 | 9/2013 | Palmroos et al. |
| 8,551,038 B2 | 10/2013 | Tsoukalis et al. |
| 8,560,345 B2 | 10/2013 | Wehba et al. |
| 8,579,884 B2 | 11/2013 | Lanier et al. |
| 8,655,676 B2 | 2/2014 | Wehba et al. |
| 8,660,860 B2 | 2/2014 | Wehba et al. |
| 8,662,388 B2 | 3/2014 | Belkin |
| 8,666,769 B2 | 3/2014 | Butler et al. |
| 8,700,421 B2 | 4/2014 | Feng et al. |
| 8,731,960 B2 | 5/2014 | Butler et al. |
| 8,768,719 B2 | 7/2014 | Wehba et al. |
| 8,771,251 B2 | 7/2014 | Ruchti et al. |
| 8,777,895 B2 | 7/2014 | Hsu et al. |
| 8,799,012 B2 | 8/2014 | Butler et al. |
| 8,876,793 B2 | 11/2014 | Ledford et al. |
| 8,922,330 B2 | 12/2014 | Moberg et al. |
| 8,952,794 B2 | 2/2015 | Bloomquist et al. |
| 9,026,370 B2 | 5/2015 | Rubalcaba et al. |
| 9,069,887 B2 | 6/2015 | Gupta et al. |
| 9,089,642 B2 | 7/2015 | Murphy et al. |
| 9,114,217 B2 | 8/2015 | Sur et al. |
| 9,123,077 B2 | 9/2015 | Silkaitis et al. |
| 9,240,002 B2 | 1/2016 | Hume et al. |
| 9,381,296 B2 | 7/2016 | Arrizza et al. |
| 9,393,362 B2 | 7/2016 | Cozmi et al. |
| 9,539,383 B2 | 1/2017 | Kohlbrecher |
| 9,572,923 B2 | 2/2017 | Howard et al. |
| 9,594,875 B2 | 3/2017 | Arrizza et al. |
| 9,604,000 B2 | 3/2017 | Wehba et al. |
| 9,641,432 B2 | 5/2017 | Jha et al. |
| 9,662,436 B2 | 5/2017 | Belkin et al. |
| 9,707,341 B2 | 7/2017 | Dumas, III et al. |
| 9,724,470 B2 | 8/2017 | Day et al. |
| 2001/0016056 A1 | 8/2001 | Westphal et al. |
| 2001/0031944 A1 | 10/2001 | Peterson et al. |
| 2001/0032099 A1 | 10/2001 | Joao |
| 2001/0037060 A1 | 11/2001 | Thompson et al. |
| 2001/0044731 A1 | 11/2001 | Coffman et al. |
| 2001/0051787 A1 | 12/2001 | Haller et al. |
| 2001/0056358 A1 | 12/2001 | Dulong et al. |
| 2002/0010595 A1 | 1/2002 | Kapp |
| 2002/0013723 A1 | 1/2002 | Mise |
| 2002/0015018 A1 | 2/2002 | Shimazu et al. |
| 2002/0019584 A1 | 2/2002 | Schulze et al. |
| 2002/0026103 A1 | 2/2002 | Norris et al. |
| 2002/0029776 A1 | 3/2002 | Blomquist |
| 2002/0032583 A1 | 3/2002 | Joao |
| 2002/0040208 A1 | 4/2002 | Flaherty et al. |
| 2002/0040282 A1 | 4/2002 | Bailey et al. |
| 2002/0082728 A1 | 6/2002 | Mueller et al. |
| 2002/0087115 A1 | 7/2002 | Hartlaub |
| 2002/0087116 A1 | 7/2002 | Hartlaub |
| 2002/0095486 A1 | 7/2002 | Bahl |
| 2002/0103675 A1 | 8/2002 | Vanelli |
| 2002/0123905 A1 | 9/2002 | Goodroe et al. |
| 2002/0152239 A1 | 10/2002 | Bautista-Lloyd et al. |
| 2002/0194329 A1 | 12/2002 | Alling |
| 2003/0009244 A1 | 1/2003 | Engleson |
| 2003/0013959 A1 | 1/2003 | Grunwald et al. |
| 2003/0014222 A1 | 1/2003 | Klass et al. |
| 2003/0025602 A1 | 2/2003 | Medema et al. |
| 2003/0028082 A1 | 2/2003 | Thompson |
| 2003/0036683 A1 | 2/2003 | Kehr et al. |
| 2003/0047126 A1 | 3/2003 | Tomaschko |
| 2003/0050621 A1 | 3/2003 | Lebel et al. |
| 2003/0059750 A1 | 3/2003 | Bindler et al. |
| 2003/0060688 A1 | 3/2003 | Ciarniello et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0106553 A1 | 6/2003 | Vanderveen |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |

(56) References Cited

U.S. PATENT DOCUMENTS

| | | |
|---|---|---|
| 2003/0212379 A1 | 11/2003 | Bylund et al. |
| 2003/0217962 A1 | 11/2003 | Childers et al. |
| 2004/0015132 A1 | 1/2004 | Brown |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |
| 2005/0086072 A1 | 4/2005 | Fox |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102669 A1 | 5/2005 | Marney et al. |
| 2005/0107923 A1 | 5/2005 | Vanderveen |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0137573 A1 | 6/2005 | McLaughlin |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox, Jr. et al. |
| 2005/0273059 A1 | 12/2005 | Mernoe et al. |
| 2005/0277873 A1 | 12/2005 | Stewart et al. |
| 2005/0277890 A1 | 12/2005 | Stewart et al. |
| 2005/0277911 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122867 A1 | 6/2006 | Eggers et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229551 A1* | 10/2006 | Martinez ............... A61M 5/172 604/67 |
| 2006/0229557 A1 | 10/2006 | Fathallah et al. |
| 2006/0229918 A1 | 10/2006 | Fotsch et al. |
| 2006/0258985 A1 | 11/2006 | Russell |
| 2006/0259327 A1 | 11/2006 | Hoag |
| 2006/0264895 A1 | 11/2006 | Flanders |
| 2006/0265186 A1 | 11/2006 | Holland et al. |
| 2006/0265246 A1 | 11/2006 | Hoag |
| 2006/0267753 A1 | 11/2006 | Hussey et al. |
| 2006/0268710 A1 | 11/2006 | Appanna et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0027506 A1 | 2/2007 | Stender et al. |
| 2007/0060796 A1 | 3/2007 | Kim |
| 2007/0060871 A1 | 3/2007 | Istoc |
| 2007/0065363 A1 | 3/2007 | Dalal et al. |
| 2007/0073419 A1 | 3/2007 | Sesay |
| 2007/0078314 A1 | 4/2007 | Grounsell |
| 2007/0083870 A1 | 4/2007 | Kanakogi |
| 2007/0088333 A1 | 4/2007 | Levin et al. |

(56) References Cited

U.S. PATENT DOCUMENTS

| | | |
|---|---|---|
| 2007/0093786 A1 | 4/2007 | Goldsmith et al. |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213598 A1 | 9/2007 | Howard et al. |
| 2007/0213657 A1 | 9/2007 | Jennewine et al. |
| 2007/0214003 A1 | 9/2007 | Holland et al. |
| 2007/0215545 A1 | 9/2007 | Bissler et al. |
| 2007/0229249 A1 | 10/2007 | McNeal et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0004904 A1 | 1/2008 | Tran |
| 2008/0009684 A1 | 1/2008 | Corsetti et al. |
| 2008/0041942 A1 | 2/2008 | Aissa |
| 2008/0052704 A1 | 2/2008 | Wysocki |
| 2008/0065417 A1 | 3/2008 | Jung et al. |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0139907 A1 | 6/2008 | Rao et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0200870 A1 | 8/2008 | Palmroos et al. |
| 2008/0214919 A1 | 9/2008 | Harmon et al. |
| 2008/0243055 A1 | 10/2008 | Fathallah et al. |
| 2008/0246748 A1 | 10/2008 | Cassidy et al. |
| 2008/0256305 A1 | 10/2008 | Kwon |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0320387 A1 | 12/2008 | Sasaki et al. |
| 2008/0320466 A1 | 12/2008 | Dias |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0051560 A1 | 2/2009 | Manning et al. |
| 2009/0054754 A1 | 2/2009 | McMahon et al. |
| 2009/0057399 A1 | 3/2009 | Sajkowsky |
| 2009/0069785 A1 | 3/2009 | Miller et al. |
| 2009/0099867 A1 | 4/2009 | Newman |
| 2009/0135196 A1 | 5/2009 | Holland et al. |
| 2009/0143662 A1 | 6/2009 | Estes et al. |
| 2009/0150174 A1 | 6/2009 | Buck et al. |
| 2009/0157695 A1 | 6/2009 | Roberts |
| 2009/0158274 A1 | 6/2009 | Roberts |
| 2009/0171289 A1 | 7/2009 | Davis et al. |
| 2009/0177146 A1 | 7/2009 | Nesbitt et al. |
| 2009/0177769 A1 | 7/2009 | Roberts |
| 2009/0177992 A1 | 7/2009 | Rubalcaba et al. |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Bloomquist et al. |
| 2009/0275896 A1 | 11/2009 | Kamen et al. |
| 2009/0284691 A1 | 11/2009 | Marhefka et al. |
| 2009/0326340 A1 | 12/2009 | Wang |
| 2009/0326516 A1 | 12/2009 | Bangera et al. |
| 2010/0022988 A1 | 1/2010 | Wochner |
| 2010/0036310 A1 | 2/2010 | Hillman |
| 2010/0056992 A1 | 3/2010 | Hayter |
| 2010/0095229 A1 | 4/2010 | Dixon et al. |
| 2010/0121170 A1 | 5/2010 | Rule |
| 2010/0121654 A1 | 5/2010 | Portnoy et al. |
| 2010/0130933 A1 | 5/2010 | Holland et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0273738 A1 | 10/2010 | Valcke et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0093284 A1 | 4/2011 | Dicks et al. |
| 2011/0099313 A1 | 4/2011 | Bolanowski |
| 2011/0125095 A1 | 5/2011 | Lebel et al. |
| 2011/0175728 A1 | 7/2011 | Baker, Jr. |
| 2011/0178462 A1 | 7/2011 | Moberg et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0011253 A1 | 1/2012 | Friedman et al. |
| 2012/0016305 A1 | 1/2012 | Jollota |
| 2012/0070045 A1 | 3/2012 | Vesper et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0130308 A1 | 5/2012 | Silkaitis et al. |
| 2012/0143116 A1 | 6/2012 | Ware et al. |
| 2012/0150556 A1 | 6/2012 | Galasso et al. |
| 2012/0179135 A1 | 7/2012 | Rinehart et al. |
| 2012/0179136 A1 | 7/2012 | Rinehart et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0277716 A1 | 11/2012 | Ali et al. |

(56) References Cited

U.S. PATENT DOCUMENTS

| | | |
|---|---|---|
| 2012/0284734 A1 | 11/2012 | McQuaid et al. |
| 2012/0323212 A1 | 12/2012 | Murphy |
| 2013/0006666 A1 | 1/2013 | Schneider |
| 2013/0006702 A1 | 1/2013 | Wu |
| 2013/0036412 A1 | 2/2013 | Birtwhistle et al. |
| 2013/0046508 A1 | 2/2013 | Sur et al. |
| 2013/0047113 A1 | 2/2013 | Ruchti et al. |
| 2013/0066265 A1 | 3/2013 | Grant et al. |
| 2013/0072872 A1 | 3/2013 | Yodfat et al. |
| 2013/0085689 A1 | 4/2013 | Sur et al. |
| 2013/0096444 A1 | 4/2013 | Condurso et al. |
| 2013/0102963 A1 | 4/2013 | Marsh et al. |
| 2013/0138452 A1 | 5/2013 | Cork et al. |
| 2013/0144206 A1 | 6/2013 | Lee et al. |
| 2013/0158504 A1 | 6/2013 | Ruchti et al. |
| 2013/0167245 A1 | 6/2013 | Birtwhistle et al. |
| 2013/0191770 A1 | 7/2013 | Bartz et al. |
| 2013/0218080 A1 | 8/2013 | Peterfreund et al. |
| 2013/0261993 A1 | 10/2013 | Ruchti et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2014/0039446 A1 | 2/2014 | Day |
| 2014/0257251 A1 | 9/2014 | Bush et al. |
| 2014/0350513 A1 | 11/2014 | Oruklu et al. |
| 2014/0358077 A1 | 12/2014 | Oruklu et al. |
| 2014/0358081 A1 | 12/2014 | Dumas et al. |
| 2014/0366878 A1 | 12/2014 | Baron |
| 2015/0005935 A1 | 1/2015 | Bae et al. |
| 2015/0058044 A1 | 2/2015 | Butler et al. |
| 2015/0066531 A1 | 3/2015 | Jacobson et al. |
| 2015/0317891 A1 | 11/2015 | Day et al. |
| 2015/0379237 A1 | 12/2015 | Mills et al. |
| 2016/0051751 A1 | 2/2016 | Silkaitis et al. |
| 2016/0350513 A1 | 12/2016 | Jacobson et al. |
| 2017/0024534 A1 | 1/2017 | Arrizza et al. |

FOREIGN PATENT DOCUMENTS

| | | |
|---|---|---|
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |
| EP | 0 652 528 | 5/1995 |
| EP | 0 672 427 | 9/1995 |
| EP | 0 683 465 | 11/1995 |
| EP | 0 880 936 | 12/1998 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| FR | 2 717 919 | 9/1995 |
| GB | 2 285 135 | 6/1995 |
| JP | 04-161139 | 6/1992 |
| JP | 2003-016183 | 1/2003 |
| JP | 2003-296173 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2008-158622 | 7/2008 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | WO 96/008755 | 3/1996 |
| WO | WO 96/025186 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/050526 | 6/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/057729 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | 20012120078 A2 | 9/2012 |
| WO | WO 2012/140547 | 10/2012 |
| WO | WO 2012/164556 | 12/2012 |
| WO | WO 2012/170942 | 12/2012 |
| WO | 2013045506 A1 | 4/2013 |

(56) References Cited

FOREIGN PATENT DOCUMENTS

| WO | WO 2014/100736 | 6/2014 |
|---|---|---|
| WO | WO 2014/131729 | 9/2014 |
| WO | WO 2014/131730 | 9/2014 |

OTHER PUBLICATIONS

Givens et al., Exploring the Internal State of User Interfaces by Combining Computer Vision Techniques with Grammatical Inference, Sikuli script, 2013, pp. 1165-1168, ICSE, San Francisco, CA.
Harmann et al., Pumpsim: A Software package for simulating computer-controlled drug infusion pumps, Annual International Conference of IEEE, Engineering in Medicine and biology Society, 1990, pp. 2019-2020, vol. 12, No. 5.
Akridge, Jeannie, "New Pumps Outsmart User Error", Healthcare Purchasing News, Apr. 2011, pp. 10, http://web.archive.org/web/20110426122450/http://www.hpnonline.com/inside/2011-04/1104-OR-Pumps.html.
Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.
Beard et al., "Total Quality Pain Management: History, Background, Resources", Abbott Laboratories, TQPM Survey History, pp. 1-3.
Bektas et al., "Bluetooth Communication Employing Antenna Diversity", Proceedings of Eight IEEE International Symposium on Computers and Communication, Jul. 2003, pp. 6.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Braun, "Infusomat® Space and Accessories", Instructions for Use, Nov. 2010, pp. 68. http://corp.bbraun.ee/Extranet/Infusioonipumbad/Kasutusjuhendid/Vand/Kazsutusjuhend-Infusomet_space(vers688J.inglise_k).pdf.
Brownlee, Seth, "Product Spotlight: the Plum A+ with Hospira MedNet Infusion System", PP&P Magazine, Dec. 2005, vol. 2, No. 7, pp. 2.
Cannon, MD et al., "Automated Heparin-Delivery System to Control Activated Partial Thromboplastin Time", Circulation, Feb. 16, 1999, vol. 99, pp. 751-756.
Cardinal Health, "Alaris® Syringe Pumps" Technical Service Manual, Copyright 2002-2006, Issue 9, pp. 1-88, http://www.frankshospitalworkshop.com/equipment/documents/infusion_pumps/service_manuals/Cardinal_Alaris-Service Manua.pdf.
Chen et al., "Enabling Location-Based Services on Wireless LANs", The 11th IEEE International Conference on Networks, ICON 2003, Sep. 28-Oct. 1, 2003, pp. 567-572.
"Computer Dictionary", Microsoft Press, Third Edition, Microsoft Press, 1997, pp. 430 & 506.
Crawford, Anne "Building a Successful Quality Pain Service: Using Patient Satisfaction Data and the Clinical Practice Guideline", Microsoft Corporation, USA, pp. 1-6.
Crocker et al., "Augmented BNF for Syntax Specifications: ABNF", Network Working Group, Standards Track, Jan. 2008, pp. 16.

Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Davies, T., "Cordless Data Acquisition in a Hospital Environment", IEE Colloquium on Cordless Computing—Systems and User Experience, 1993, pp. 4.
Dayhoff et al., "Medical Data Capture and Display: The Importance of Clinicians' Workstation Design", AMIA, Inc., 1994, pp. 541-545.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
East PhD et al., "Digital Electronic Communication Between ICU Ventilators and Computers and Printers", Respiratory Care, Sep. 1992, vol. 37, No. 9, pp. 1113-1122.
Einhorn, George W., "Total Quality Pain Management: A Computerized Quality Assessment Tool for Postoperative Pain Management", Abbott Laboratories, Chicago, IL, Mar. 2, 2000, pp. 1-4.
Eskew et al., "Using Innovative Technologies to Set New Safety Standards for the Infusion of Intravenous Medications", Hospital Pharmacy, 2002, vol. 37, No. 11, pp. 1179-1189.
Felleiter et al., "Data Processing in Prehospital Emergency Medicine", International journal of Clinical Monitoring and Computing, Feb. 1995, vol. 12, No. 1, pp. 37-41.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Gage et al., "Automated Anesthesia Surgery Medical Record System", International Journal of Clinical Monitoring and Computing, Dec. 1990, vol. 7, No. 4, pp. 259-263.
Galt et al., "Personal Digital Assistant-Based Drug Information Sources: Potential to Improve Medication Safety", Journal of Medical Library Association, Apr. 2005, vol. 93, No. 2, pp. 229-236.
Gardner, Ph.D. et al., "Real Time Data Acquisition: Recommendations for the Medical Information Bus (MIB)", 1992, pp. 813-817.
"General-Purpose Infusion Pumps", Health Devices, EXRI Institute, Oct. 1, 2002, vol. 31, No. 10, pp. 353-387.
Glaeser, "A Hierarchical Minicomputer System for Continuous Post-Surgical Monitoring", Computers and Biomedical Research, Aug. 31, 1975, pp. 336-361.
Goldberg et al., "Clinical Results of an Updated Insulin Infusion Protocol in Critically Ill Patients", Diabetes Spectrum, 2005, vol. 18, No. 3, pp. 188-191.
Gomez et al., "CLAM: Connection-Less, Lightweight, and Multiway Communication Support for Distributed Computing", Computer Science, 1997, vol. 1199, pp. 227-240.
Graseby, "Model 3000/500 and Micro 3100/505: Volumetric Infusion Pump", Technical Service Manual, Graseby Medical Ltd., Apr. 2002, Issue A, pp. 160.
Graseby, "Model 3000/500 and Micro 3100/505: Volumetric Infusion Pump: Illustrated Parts List for Pump Serial Numbers from 3000 to 59,999", Technical Service Manual, Graseby Medical Ltd., Apr. 2002, Issue A, pp. 71.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hasegawa et al., "On a Portable Memory Device for Physical Activities and Informations of Maternal Perception", Journal of Perinatal Medicine, 1988, vol. 16, No. 4, pp. 349-356.
Hawley et al., "Clinical Implementation of an Automated Medical Information Bus in an Intensive Care Unit", Proceedings of the Annual Symposium on Computer Application in Medical Care, Nov. 9, 1988, pp. 621-624.
Hayes-Roth et al., "Guardian: A Prototype Intelligent Agent for Intensive-Care Monitoring", Artificial Intelligence in Medicine, vol. 4, Dec. 31, 1992, pp. 165-185.
Hospira, GemStar® Pain Management Infusion System 9-084-PR1-2-2, www.hospira.com/products/gemstar_painmanagement.aspx, Jan. 28, 2010, pp. 1-2.
Introducing Abbott TQPM (Total Quality Pain Management), Abbott Laboratories, Abbott Park, IL, May 2000, pp. 1-4.

(56) References Cited

OTHER PUBLICATIONS

Isaka et al., "Control Strategies for Arterial Blood Pressure Regulation", IEEE Transactions on Biomedical Engineering, Apr. 1993, vol. 40, No. 4, pp. 353-363.
Johnson et al., "Using BCMA Software to Improve Patient Safety in Veterans Administration Medical Centers", Journal of Healthcare Information Management, Dec. 6, 2004, vol. 16, No. 1, pp. 46-51.
Kent Displays, "Reflex™ Electronic Skins", Product Brief 25127B, 2009, pp. 2.
Kent Displays, "Reflex Electronic Skins Engineering Evaluation Kit", 25136A, Mar. 10, 2009.
Lefkowitz et al., "A Trial of the Use of Bar Code Technology to Restructure a Drug Distribution and Administration System", Hospital Pharmacy, Mar. 31, 1991, vol. 26, No. 3, pp. 239-242.
Lenssen et al., "Bright Color Electronic Paper Technology and Applications", IDS '09 Publication EP1-2 (Phillips Research), 2009, pp. 529-532.
Cardinal Health, "Alaris® Syringe Pumps" Technical Service Manual, Copyright 2002-2006, Issue 9, pp. 1-88, http://www.frankshospitalworkshop.com/equipment/documents/infusion_pumps/service_manuals/Cardinal_Alaris-Service Manual.pdf.
Linkens, D.A. "Computer Control for Patient Care", Computer Control of Real-Time Processes, IEE Control Engineering Series 41, 1990, Ch. 13, pp. 216-238.
Mako Hill et al., "The Official Ubuntu Book", Shoeisha Co., Ltd., 1st Edition, Jun. 11, 2007, pp. 115 to 125.
Marshall, et al., "New Microprocessor—Based Insulin Controller", IEEE Transactions on Biomedical Engineering, Nov. 1983, vol. BME-30, No. 11, pp. 689-695.
Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.
Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Medfusion™, "Medfusion Syringe Infusion Pump Model 4000", Operator's Manual, Software Version V1.1, Sep. 2011, pp. 154. http://www.medfusionpump.com/assets/literature/manuals/Operators_Manual 4000_40-5760-51A.pdf.
Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.
Micrel Medical Devices, "MP Daily +" http://web.archive.org/web/20130803235715/http://www.micrelmed.com/index.aspx?productid=9 as archived Aug. 3, 2013 1 page.
Moghissi, Etie, MD, FACP, FACE, "Hyperglycemia in Hospitalized Patients", A Supplement to ACP Hospitalist, Jun. 15, 2008, pp. 32.
Murray, Jr. et al., "Automated Drug Identification System (during surgery)", IEEE Proceedings of Southeastcon '91, Apr. 7-10, 1991, pp. 265.
Nicholson et al., "'Smart' Infusion Apparatus for Computation and Automated Delivery of Loading, Tapering, and Maintenance Infusion Regimens of Lidocaine, Procainamide, and Theophylline", Proceedings of The Seventh Annual Symposium on Computer Applications in Medical Care, Oct. 1983, pp. 212-213.
Nolan et al., "The P1073 Medical Information Bus Standard: Overview and Benefits for Clinical Users", 1990, pp. 216-219.
O'Shea, Kristen L., "Infusion Management: Working Smarter, Not Harder", Hospital Pharmacy, Apr. 2013, vol. 48, No. 3, pp. S1-S14.
Package Management in Debian GNU/Linux, Debian GNU/Linux Expert Desktop Use Special, Giutsu-Hyohron Co., Ltd., First Edition, Sep. 25, 2004, pp. 183-185.

Passos et al., "Distributed Software Platform for Automation and Control of General Anaesthesia", Eighth International Symposium on Parallel and Distributed Computing, ISPDC '09, Jun. 30-Jul. 4, 2009, pp. 8.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.
Ritchie et al., "A Microcomputer Based Controller for Neuromuscular Block During Surgery", Annals of Biomedical Engineering, Jan. 1985, vol. 13, No. 1, pp. 3-15.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sanders et al., "The Computer in a Programmable Implantable Medication System (PIMS)", Proceedings of the Annual Symposium on Computer Application in Medical Care, Nov. 2, 1982, pp. 682-685.
Schulze et al., "Advanced Sensors Technology Survey", Final Report, Feb. 10, 1992, pp. 161.
Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D., "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically III Patients", Proceedings of the IEEE, Sep. 1979, vol. 67, No. 9, pp. 1300-1306.
"SIGMA Spectrum: Operator's Manual", Oct. 2009, pp. 72. http://static.medonecapital.com/manuals/userManuals/Sigma-Spectrum-Operator-Manual-October-2009.pdf.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. http://www.thomasland.com/hpi4209-832.pdf.
Slack, W.V., "Information Technologies for Transforming Health Care", https://www.andrew.cmu.edu/course/90-853/medis.dir/otadocs.dir/03ch2.pdf, ch. 2, 1995, pp. 29-78.
Sodder, Lisa, "A Center Keeps Medicine in Right Hands", Dec. 4, 1999, pp. 1-2.
Stitt, F.W., "The Problem-Oriented Medical Synopsis: a Patient-Centered Clinical Information System", Proceedings of the Annual Symposium on Computer Application in Medical Care, 1994, pp. 88-92.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.

(56) References Cited

OTHER PUBLICATIONS

Szeinbach et al., "Automated Dispensing Technologies: Effect on Managed Care", Journal of Managed Care Pharmacy (JMCP), Sep./Oct. 1995, vol. 1, No. 2, pp. 121-127.

Szolovits et al., "Guardian Angel: Patient-Centered Health Information Systems", Technical Report MIT/LCS/TR-604, Massachusetts Institute of Technology Laboratory for Computer Science, May 1994, pp. 39.

Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.

Van Den Berghe, M.D., Ph.D., et al., "Intensive Insulin Therapy in the Medical ICU", The New England Journal of Medicine, Feb. 2, 2006, vol. 354, No. 5, pp. 449-461.

Van Der Maas et al., "Requirements for Medical Modeling Languages", Journal of the American Medical Informatics Association, Mar./Apr. 2001, vol. 8, No. 2, pp. 146-162.

Villalobos et al., "Computerized System in Intensive Care medicine", Medical Informatics, vol. 11, No. 3, 1986, pp. 269-275.

Wilkins et al., "A Regular Language: The Annotated Case Report Form", PPD Inc., PharmaSUG2011—Paper CD18, 2011, pp. 1-9.

Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.

Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.

Yurkonis et al., "Computer Simulation of Adaptive Drug Infusion", IEEE Transactions on Biomedical Engineering, vol. BME-34, No. 8, Aug. 1987, pp. 633-635.

Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.

\* cited by examiner

INFUSION PUMP AUTOMATION SYSTEM AND METHOD

BACKGROUND OF THE INVENTION

Field of the Invention

One or more embodiments of the invention are related to the field of infusion pump automation and execution of one or more commands generated and triggered remotely. Specifically, one or more embodiments relate to a system and method of qualifying whether one or more commands, prior to executing such commands, may be successfully executed based on a desired infusion state of an infusion pump, a current infusion state of the infusion pump, and a current infusion pump user interface state.

Description of the Related Art

Current solutions for automated medication delivery systems typically involve devices with three main components; a diagnostic device or sensor, a closed-loop control algorithm and an infusion system. Such devices, generally, may be integrated to be part of a distributed system that communicates in a continuous or periodic manner. In using a continuous or periodic manner of communication, typically, the infusion system may involve any number of delivery routes, such as intravenous or subcutaneous routes. Furthermore, using current solutions, the three main device components are usually managed by a higher-level coordination software system that ensures one or more events occur in an appropriate manner.

For example, one typical system for automated medication delivery includes an artificial pancreas or closed-loop control system for managing glucose, wherein insulin levels are automatically adjusted based on a patient's glucose level that may be observed over time. In using such a system, generally, adjustment is directed by an adaptive control system that uses an error factor between observed glucose values and desired glucose values in order to calculate the insulin and/or nutrition quantities that are to be delivered over time. Other similar systems are used for anti-coagulation management, pain management, fluid management, control of cardiovascular parameters and sedation management.

Another example of a current automated medication delivery system typically uses remote commands to initialize an IV infusion, change parameters of the IV infusion, or modify the state of the IV infusion. In such a system, for example, the commands are generated by a caregiver using an input device, or using a computerized decision support system designed to achieve a particular therapeutic objective.

For example, United States Patent Publication 2010/0095229 to Dixon et al., entitled "Graphical User Interface for Glucose Monitoring System", discloses a graphical user interface for control of glucose with navigational aids, wherein a user may navigate between icons and select one or more outputs that display glucose data. However, the system appears to lack any teaching or suggestion of an infusion pump automated system that may accept commands to change an infusion state of the infusion pump, and determine if the commands are consistent with a current infusion state of the infusion pump in order to be executed successfully.

United States Patent Publication 20070213598 to Howard et al., entitled "System for Maintaining Drug Information and Communicating with Medication Delivery devices", discloses a system for maintaining drug data and communicating with delivery devices. However, the system appears to lack any teaching or suggestion of an infusion pump automated system that may accept commands to change an infusion state of the infusion pump, and determine if the commands are consistent with a current infusion state of the infusion pump in order to be executed successfully.

United States Patent Publication 20080320387 to Sasaki et al., entitled "Information Displaying Device and Information Displaying Method", discloses an information displaying device related to analyzing a graphical user interface screen, to store and manage displayed information for analysis of specified information. The system of Sasaki et al. appears to lack any teaching or suggestion of an infusion pump automated system that may accept commands to change an infusion state of the infusion pump, and determine if the commands are consistent with a current infusion state of the infusion pump in order to be executed successfully.

United States Patent Publication 20080041942 to Aissa, entitled "Biometric Multi-Purpose Terminal, Payroll and Work Management System and Related Methods", discloses a biometric terminal that uses a fingerprint reader, or other biometric information from a user, in order to authenticate the user, and as such provides security. The system and related methods, however, appear to lack any teaching or suggestion of an infusion pump automated system that may accept commands to change an infusion state of the infusion pump, and determine if the commands are consistent with a current infusion state of the infusion pump in order to be executed successfully.

United States Patent Publication 20100121170 to Rule, entitled "Fluid Component Analysis System and Method for Glucose Monitoring and Control", discloses methods and systems for determining concentrations in a sample, such as bodily fluid, for glycemic control. For example, elements of Rule are related to glucose management and patient dosing via a remote communication interface. The systems and methods, however, appear to lack any teaching or suggestion of an infusion pump automated system that may accept commands to change an infusion state of the infusion pump, and determine if the commands are consistent with a current infusion state of the infusion pump in order to be executed successfully.

United States Patent Publication 20010051787 to Haller et al., entitled "System and Method of Automated Invoicing for Communications Between an Implantable Medical Device and a Remote Computer System or Health Care Provider", discloses a system for automatically generating invoices for medical services provided to a patient, where, for example, an implantable medical device is capable of communicating with a communication module, mobile telephone, a means for generating an invoice and a remote computer system. Although the communication module and/or mobile telephone may receive information from the implantable medical device or relay the information thereto, the system appears to lack any teaching or suggestion of an infusion pump automated system that may accept commands to change an infusion state of the infusion pump, and determine if the commands are consistent with a current infusion state of the infusion pump in order to be executed successfully.

U.S. Pat. No. 7,835,927 to Schlotterbeck et al., entitled "Medication Management System", discloses a system and method for confirming a medication administration has been correctly programmed, such that a medical database carrier may compare delivery parameters of the medication entered into a medication administration device in order to ensure the medication is delivered in according with medical guidelines. Although information of medication delivery may be communicated between a control system and a caregiver facility, the system of Schlotterbeck et al. appears to lack any teaching or suggestion of an infusion pump automated system that may accept commands to change an infusion state of the infusion pump, and determine if the commands are consistent with a current infusion state of the infusion pump in order to be executed successfully.

For example, United States Patent Publication 20010031944 to Peterson et al., entitled "Drug Pump Systems and Methods", is directed towards a drug pump system and method, for example, including a computer for remote communication and control of a drug pump that uses a closed loop system for automated testing of the drug pump. The computer, for example, may also simulate the drug pump for training purposes, reprogram the drug pump and test for the operation of the drug pump. In addition, it appears as though data is transferred to and from the drug pump. However, it appears as though the system of Peterson et al. does not disclose or suggest executing infusion commands based on a state of an infusion pump and state of an infusion pump user interface, does not discloses or suggest determining whether the infusion pump is able to execute the command and confirming whether the command has been executed safely and successfully.

In summary, known systems generally include analyzing a graphical user interface; however, using known systems, for example, execution of one or more unqualified commands by an IV infusion pump could be inconsistent, impossible or result in significant safety and security risks. There are no known infusion pump systems that use current infusion pump states and current user interface states to determine whether one or more commands, generated remotely, are qualified to be safely and successfully executed, for example, to change an infusion state of the infusion pump and infusion therapy thereof. For at least the reasons described above there is a need for infusion pump automation system and method.

BRIEF SUMMARY OF THE INVENTION

One or more embodiments described in the specification are related to an infusion pump automation system and method including an infusion pump having an infusion pump user interface and associated infusion pump infusion state and infusion pump user interface state, and a remote processor. In at least one embodiment of the invention, the remote processor is remote to the infusion pump and includes a controller interface and a controller coupled with the controller interface.

In one or more embodiments, the controller may bidirectionally communicate with the infusion pump, determine a current infusion state of the infusion pump and a current infusion pump user interface state and accept a command to change the infusion state of the infusion pump, for example to a desired infusion state. In addition, by way of one or more embodiments of the invention, the controller may determine if the command to change the infusion state of the infusion pump is consistent with the current infusion state of the infusion pump and consistent with the current infusion pump user interface state. The controller may then execute the command to change the infusion state of the infusion pump if the command to change the infusion state of the infusion pump is able to be successfully executed based on the command, the current infusion state of the infusion pump and the current infusion pump user interface state. The controller may then confirm that the command is successfully executed. In one or more embodiments, the command may be generated from an external server, wherein the external server is remote to the controller.

In at least one embodiment, the controller may associate the infusion pump with a medication, a dose and a patient, and, for example, in one or more embodiments, the command to change the infusion state of the infusion pump may include a medication, a dose and a patient. Furthermore, in at least one embodiment, the controller may translate the command into an infusion specific command associated with a particular type of infusion pump, for example, using a translator. In one or more embodiments of the invention, the controller may display the command on the infusion pump user interface, accept a confirmation input button request from the infusion pump, and send a simulated button press command to the infusion pump to initiate infusion or any combination thereof. By way of one or more embodiments, the controller may also, or alternatively, obtain input from the infusion pump user interface, from a user, to enable manual control takeover of the infusion pump. In at least one embodiment, the controller may authenticate a user before the execution of the command.

In one or more embodiments, the controller may log infusion status to a log file. For example, the controller may log infusion status at a conclusion of a duration of the infusion, wherein the duration of the infusion may be a predefined value, for example approximately 5 minutes. It is noted, however, that the duration of the infusion, as one of ordinary skill in the art would appreciate, may be more or less than 5 minutes, depending on a type of infusion.

In at least one embodiment of the invention, the controller may also associate the infusion pump with at least two pump channels, and verify the medication on each of the at least two pump channels.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

An infusion pump automated system and method will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
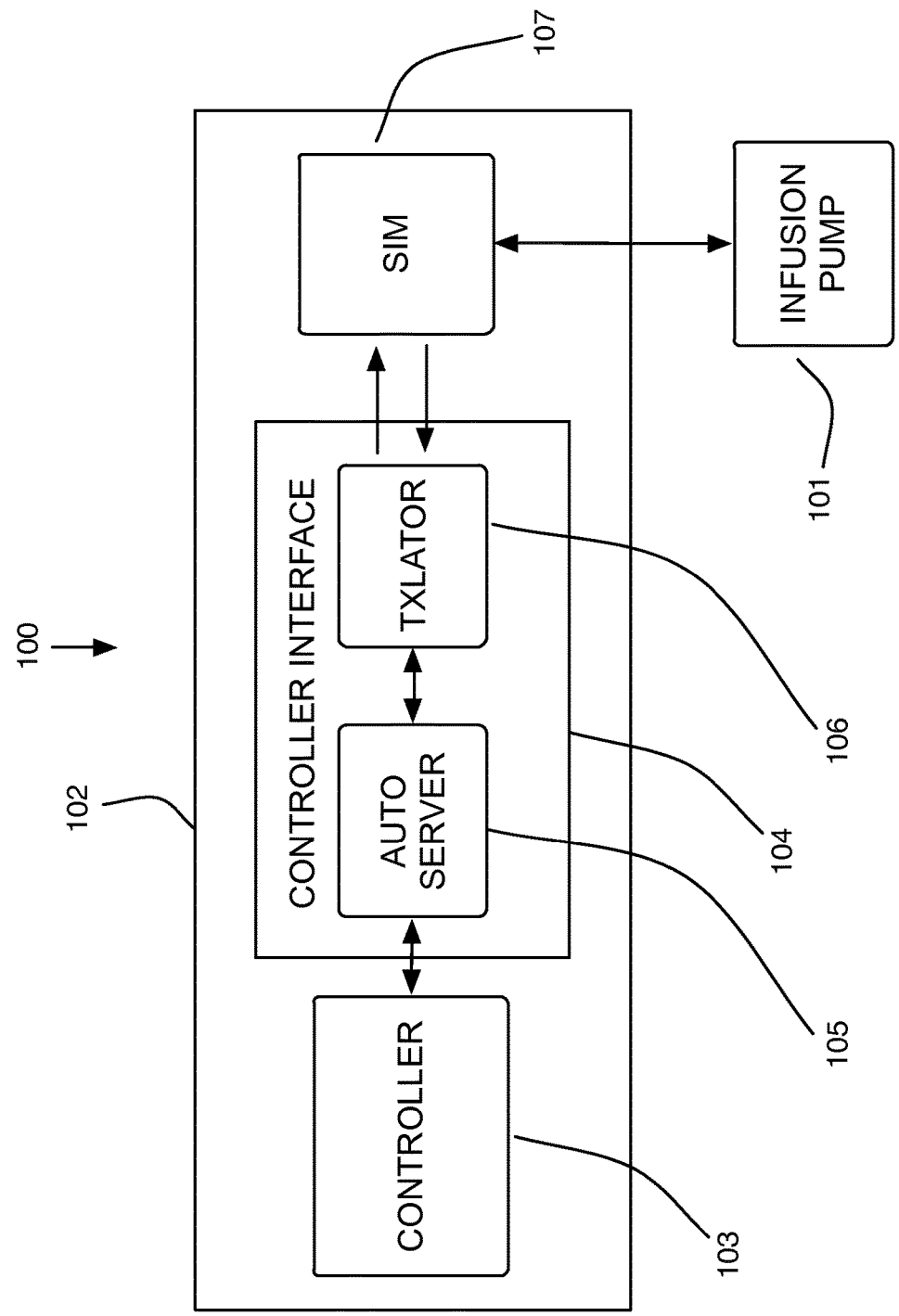
FIG. 1 illustrates an architectural view of at least one embodiment of the system.

FIG. 1 illustrates an architectural view of at least one embodiment of the system. As shown in FIG. 1, one or more embodiments of the invention include an infusion pump automation system 100 including an infusion pump 101 having an infusion pump user interface (see FIG. 4) and associated infusion pump infusion state and infusion pump user interface state, and a remote processor 102. In at least one embodiment of the invention, the remote processor is remote to the infusion pump and includes a controller interface 104 and a controller 103 coupled with the controller interface 104. By way of one or more embodiments of the invention, the controller interface 104 may include a custom printed circuit board (PCB) and a controller interface software that may enable direct control of the infusion pump 101, such as infusion pump 101 hardware, using the software running on the remote processor 102. In one or more embodiments a simulator 107 may be utilized to provide a localized interface for different types of infusion pumps and so as to translate HTTP/XML based or any other types of commands such as binary commands to Internet Protocol (IP) or other commands or protocols that the infusion pump may interface with.

In one or more embodiments, the controller 103 may bidirectionally communicate with the infusion pump 101, determine a current infusion state of the infusion pump 101 and a current infusion pump user interface state and accept a command to change the infusion state of the infusion pump 101. In addition, by way of one or more embodiments of the invention, the controller 103 may determine if the command to change the infusion state of the infusion pump 101 is consistent with the current infusion state of the infusion pump 101 and consistent with the current infusion pump user interface state. If so the controller may execute the command to change the infusion state of the infusion pump 101 if the command to change the infusion state of the infusion pump 101 is able to be successfully executed based on the command, the current infusion state of the infusion pump and the current infusion pump user interface state. The controller may also confirm that the command is successfully executed. In one or more embodiments, the command may be generated locally within the processor 102 via simulator 107 or via an external server (as discussed regarding FIG. 3 below), wherein the external server is remote to the processor 102 and wherein the external server may be a patient and/or healthcare provider system. In one or more embodiments, the generated command, as generated from the external server, may include one or more files stored in a specified directory, wherein the external server, automatically or manually via a user and/or healthcare provider may write the one or more files including the patient, medication, dose and pump channel data. In one or more embodiments, the one or more files may include an Extensible Markup Language (XML) file. For example, the user may input a user identification and infusion pump identification bar code in the one or more files. In one or more embodiments, the files, such as the XML files, may be communicated via HTTP post requests and responses or in any other manner or using any other communications protocol.

In at least one embodiment, the controller 103 may associate the infusion pump 101 with a medication, a dose and a patient, and, for example, in one or more embodiments, the command to change the infusion state of the infusion pump 101 may include a medication, a dose and a patient. In one or more embodiments, the medication may include one or more of insulin and dextrose for example. Furthermore, in at least one embodiment, the controller 103 may translate the command into an infusion specific command associated with a particular type of infusion pump, for example, using a bridge or translator 106 as part of the controller interface 104. In at least one embodiment, the controller interface 104 may also include an automation server 105. The automation server 105, for example, may bidirectionally communicate with the controller 103, the translator 106 and the infusion pump 101 via the simulator 107 for example in order to poll one or more directories from one or more of the infusion pump 101, the controller 103 and the external server to detect one or more written files, commands and data associated with the one or more commands, or any combination thereof. The automation server may communicate the files, commands and/or data to determine if the infusion pump 101 is in an appropriate mode for communication and/or the desired infusion.

In one or more embodiments of the invention, the controller 103 may display the command on the infusion pump user interface, using a display such as a touch screen display, accept a confirmation input button request from the infusion pump 101, and send a simulated button press command to the infusion pump 101 to initiate infusion. In at least one embodiment of the invention, the infusion pump 101 may immediately and automatically execute a specified program from within the infusion pump 101, such as using a drug library included in the infusion pump 101 hardware and/or software, associated with the generated command. By way of one or more embodiments, the controller 103 may in addition to, or alternatively, obtain input from the infusion pump user interface, from a user, to enable manual control takeover of the infusion pump 101. In at least one embodiment, the controller 103 may authenticate a user before the execution of the command.

In one or more embodiments, the controller 103 may log infusion status to a log file, wherein the log files may be transferred to a specified directory. For example, the controller may log infusion status at a conclusion of a duration of the infusion, wherein the duration of the infusion may be any predefined value, for example approximately 5 minutes. In at least one embodiment, the log infusion status may include volume of medication infused. Once the infusion has been activated, by the remote processor 102 for example in one or more embodiments, the infusion may not be interrupted, except via the infusion pump user interface, from one or more users, such as one or more healthcare providers. It is noted, however, that the duration of the infusion, as one of ordinary skill in the art would appreciate, may be more or less than 5 minutes or any other value, depending on a type of infusion.

In at least one embodiment of the invention, the controller 103 may associate the infusion pump 101 with at least two pump channels, and verify the medication on each of the at least two pump channels. In at least one embodiment, verification of the medication on each of the at least two pump channels may be done manually, from a user such as a healthcare provider. As such, for example, in one or more embodiments, the automation server 105 may communicate the one or more files, log files, commands and data to one or more appropriate channels of the at least two pump channels via simulator 107 to confirm that the infusion pump 101 is in an appropriate mode for communication and/or the desired infusion.

Figure 2:
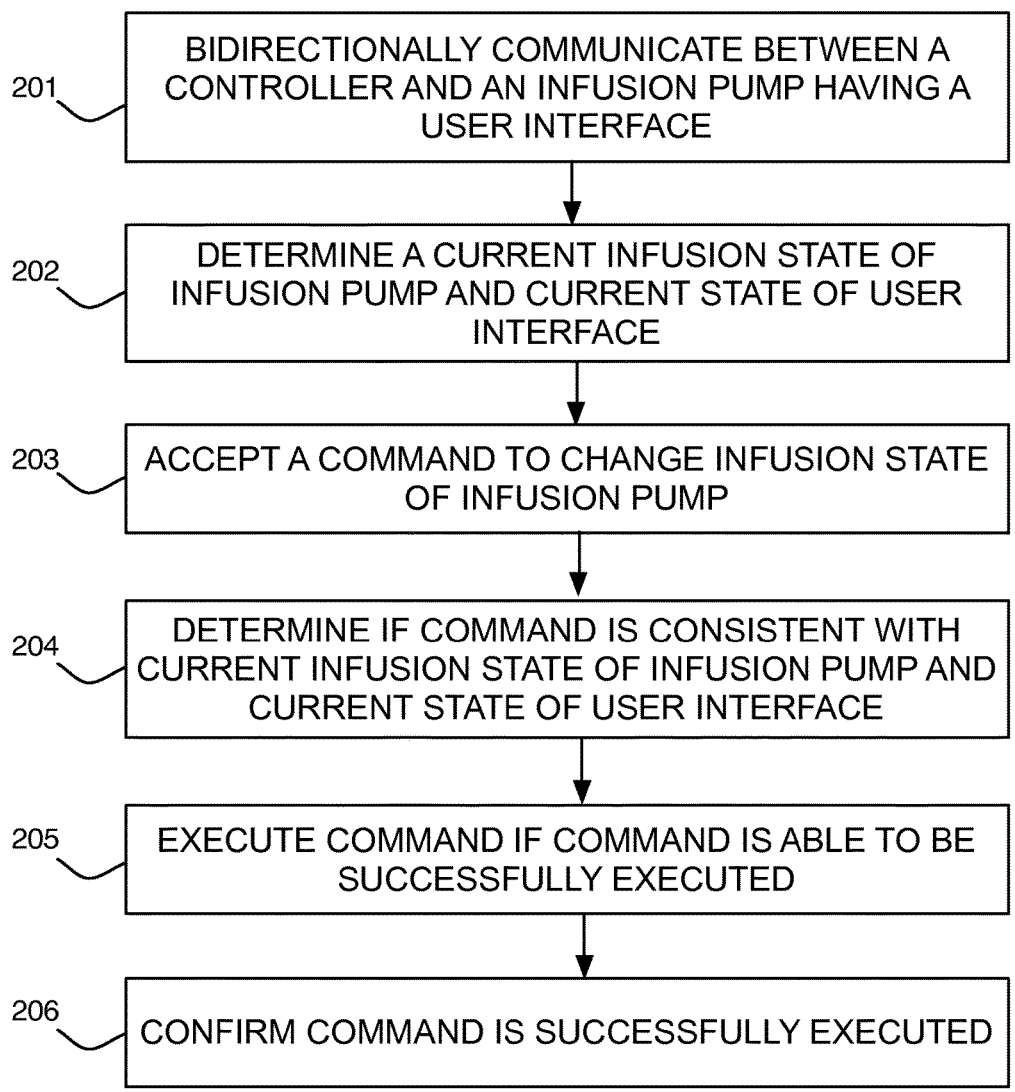
FIG. 2 illustrates a flow chart for the main elements of the system and method.

FIG. 2 illustrates a flow chart for the main elements of the system and method. As shown in FIG. 2, at 201, the controller 103 may bidirectionally communicate with the infusion pump 101 having a user interface and determine a current infusion state of the infusion pump 101 and a current infusion pump user interface state at 202. Furthermore, in at least one embodiment, the controller may accept a command to change the infusion state of the infusion pump 101 at 203, and determine if the command to change the infusion state of the infusion pump 101 is consistent with the current infusion state of the infusion pump and consistent with the current infusion pump user interface state at 204. By way of one or more embodiments, the controller 103 may execute the command to change the infusion state of the infusion pump 101 if the command to change the infusion state of the infusion pump 101 is able to be successfully executed based on the command, the current infusion state of the infusion pump 101 and the current infusion pump user interface state, at 205, and confirm that the command is successfully executed at 206. For example embodiments of the invention may check the user interface of the infusion pump as a sanity check to determine if the state of the infusion pump is reflected in the infusion pump user interface and/or visa versa. This level of robust determination of the state of an infusion pump before implementing a desired infusion is unknown in the art and may save lives by checking the user interface and infusion state before attempting to implement an infusion that may be dangerous based on the current infusion for example.

Figure 3:
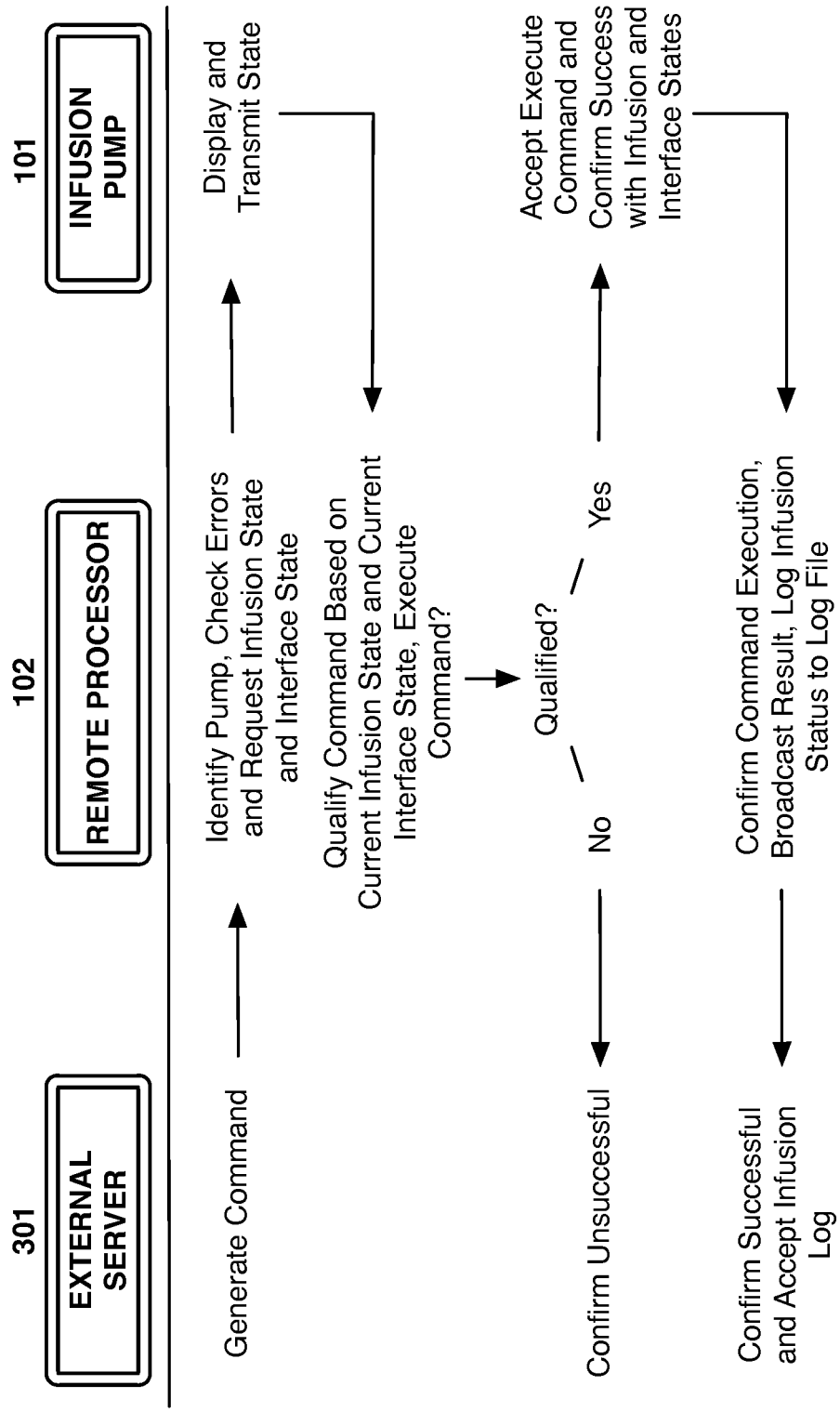
FIG. 3 illustrates a flow diagram for the main functional elements of the system and method.

FIG. 3 illustrates a flow diagram for the main functional elements of the system and method. As shown in FIG. 3, the system 100 may further include an external server 301. The external server 301, in at least one embodiment, is in communication with the remote processor 102 and the infusion pump 101. It is noted however that the communication between the external server 301, the remote processor 102 and the infusion pump 101 may include bidirectional communication, as one of ordinary skill in the art would appreciate. As shown in FIG. 3, the external server 301, by way of one or more embodiments, may generate a command to change an infusion state of the infusion pump 101 that is relayed and transmitted to the remote processor 102 for example using a communication interface (not shown). The communication interface, in one or more embodiments of the invention, may include one or more of a wireless communication interface and/or a hard-wired communication interface. In at least one embodiment, the remote processor 102 may identify the infusion pump 101, check for any errors that may currently be present and associated with the external server 301 and/or the infusion pump 101. Such errors may include, for example, one or more of a communication error, a connection error, a low-power error, an infusion error, an adaptability error or any combination thereof. In one or more embodiments, the remote processor 102 may request the infusion pump infusion state and infusion pump user interface state from the infusion pump 101. Data from the remote processor 102 is then relayed and transmitted to the infusion pump 101, for example using one or more communication interfaces as discussed above. The infusion pump 101, in at least one embodiment, may display the infusion pump infusion state and infusion pump user interface state, transmit and relay the displayed information to the remote processor 102. By way of one or more embodiments, the infusion pump 101 may receive the generated command and request confirmation via the touch screen from a user or healthcare provider, for example, for manual confirmation.

In one or more embodiments, the remote processor 102 determined whether to qualify the command as generated from the external server 301 based on the infusion pump infusion state and infusion pump user interface state as relayed and transmitted from the infusion pump 101. Qualification of the generated command, in at least one embodiment, is based on whether the generated command is able to be successfully and safely executed by the infusion pump 101 and/or by the external server 301. The remote processor 102, for example, may then determine if the generated command does qualify or does not qualify, using the controller 103. If the generated command does not qualify, in at least one embodiment, the remote processor 102 may relay and transmit an unsuccessful qualification signal, such as a text-based message or software code, to the external server 301, wherein the external server 301 may then confirm that the generated command is unsuccessful. If the generated command does qualify, in at least one embodiment, the remote processor 102 may relay and transmit a successful qualification signal, such as a text-based message or software code, and execute the generated command to the infusion pump 101. In one or more embodiments, the qualification signals may also comprise one or more of a sound alert, a vibratory alert, a visual alert, and a picture message, or any combination thereof.

By way of one or more embodiments, the infusion pump 101 may accept the generated command, and confirm that the generated command to change the infusion state of the infusion pump 101 may be successfully and safely executed by the infusion pump 101 given the current infusion pump infusion state and infusion pump user interface state. In at least one embodiment, the infusion pump 101 may relay and transmit the accepted generated command and successful infusion status or results to the remote processor 102, wherein the remote processor 102 may confirm the command execution by the infusion pump 101, broadcast the results to one or more of the infusion pump 101, the external server 301, or any other user device that may be in direct or indirect communication with the remote processor 102. In at least one embodiment, the remote processor 102, using the controller 103 for example, may log infusion status to one or more log files, and relay and transmit the successful command execution, the broadcasted results and the one or more infusion status log files to the external server 301. By way of one or more embodiments, the external server 301 may accept and confirm the successful command execution, the broadcasted results and the one or more infusion status log files.

In at least one embodiment of the invention, the system may include navigational awareness and may read the infusion pump user interface screen and verify that the system is consistent with the generated command. In one or more embodiments of the invention, the system and method enable independent evaluation of the infusion pump 101 infusion state, thus enhancing infusion and infusion pump 101 security. In addition, embodiments of the invention, using the remote processor 102 for example, may independently confirm that a command was successfully executed on the infusion pump 101. In addition, embodiments of the invention determine whether the infusion pump 101 is in a suitable state for receiving a generated command, minimizing any failures that may occur if the infusion pump 101 is in an incorrect state, as would be displayed using the infusion pump user interface and/or via the transmitted and relayed information. As such, using embodiments of the invention, the system may determine whether a generated command and auto programming of the infusion pump 101 may be accomplished, without changing or modifying the infusion pump software.

Figure 4:
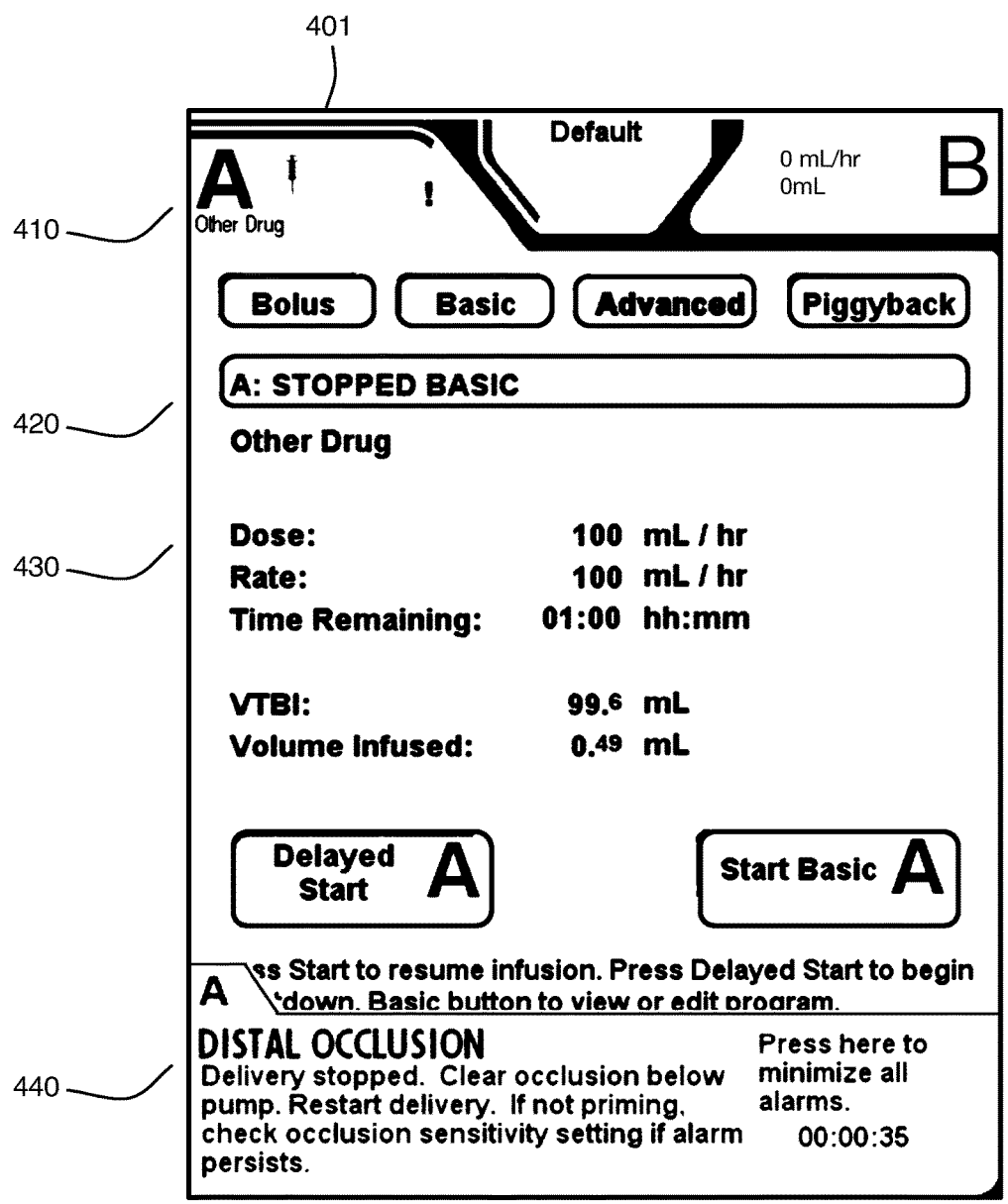
FIG. 4 illustrates an exemplary user interface of an infusion pump shown in FIG. 1.

FIG. 4 illustrates an exemplary user interface of an infusion pump. As shown, user interface 401 includes status areas 410 showing for example a type of drug and/or infusion rates or warnings if the infusion is stopped. A secondary or piggyback drug may be shown on the right side of the interface for example drug "B". Status area 420 may show the current infusion state, here shown as STOPPED. Status area 430 may show the dose and rate and/or time remaining for example and may also show any volume to be infused (VTBI), total volume infused or any other information related to the current infusion. Status area 440 may show an alarm condition, here a "Distal Occlusion". The current infusion state may include any combination of these values for example and may be obtain either directly from the infusion pump or via translation of the infusion pump user interface into any type data for transmission to the controller. For example, in one or more embodiments, the infusion pump user interface state may be translated via optical character recognition or from reading binary values in memory and converting the information to a format that is either human readable or machine readable. In one or more embodiments, the user interface state may be converted to text, HTML, XML, or any other format. As shown in user interface 401, an example text conversion embodiment may produce the following text based message for transmission to the controller.

TABLE 1

Infusion Pump User Interface State Embodiment

PrsCmnWindow ID(2): (MainWindow) BEGIN DUMP
  PrsWdgAlarmManager - ID(361): AlarmManager BEGIN DUMP
    PrsWdgAlarmDisplay - ID(1305): Alarm1Button BEGIN DUMP
      PrsWdgAlarmDisplay - Channel ID: A
      PrsWdgAlarmDisplay - Error Code:
      PrsWdgAlarmDisplay - Base Text:   DISTAL OCCLUSION
      PrsWdgAlarmDisplay - Analysis Text: Delivery stopped.
      PrsWdgAlarmDisplay - Remedy Text:   Clear occlusion below pump. Restart delivery. If
not priming, check occlusion sensitivity setting if alarm persists.
      PrsWdgAlarmDisplay - Detail Text:   Delivery stopped. Clear occlusion below pump.
Restart delivery. If not priming, check occlusion sensitivity setting if alarm persists.
      PrsWdgAlarmDisplay - Urgency: High
      PrsWdgAlarmDisplay - User Action: Press here to minimize all alarms.
      PrsWdgAlarmDisplay - Elapsed Time: 00:01:03
    PrsWdgAlarmDisplay - ID(1305): Alarm1Button END DUMP
  PrsWdgAlarmManager - ID(361): AlarmManager END DUMP
  PrsCmnWindow ID(7): (AchannelWindow) BEGIN DUMP
    PrsWdgHelpTextArea - ID(310): HelpTextArea BEGIN DUMP
      PrsWdgPrompt - ID(424): HelptextLine1Prompt - Text: Press Start to resume infusion.
Press Delayed Start to begin
      PrsWdgPrompt - ID(425): HelptextLine2Prompt - Text: countdown. Basic button to view
or edit program.
      PrsWdgPrompt - ID(426): HelptextLine3Prompt - Text:
    PrsWdgHelpTextArea - ID(310): HelpTextArea END DUMP
    PrsCmnWindow ID(8): (TherapyWindow) BEGIN DUMP
      PrsCmnWindow ID(38): (BasicTherapyStoppedWindow) BEGIN DUMP
        PrsWdgPrompt - ID(615): NearViewDoseTitlePrompt - Text: Dose:
        PrsWdgPrompt - ID(626): NearViewDoseUnitsPrompt - Text: mL/hr
        PrsWdgPrompt - ID(614): NearViewDosePrompt - Text: 100
        PrsWdgChannelButton - ID(1526): DelayedStartButton - Status: ACTIVE Text: Delayed
Start A
        PrsWdgChannelButton - ID(1525): StartProgramButton - Status: ACTIVE Text: Start
Basic A
        PrsWdgPrompt - ID(632): NearViewVolumeInfusedTitlePrompt - Text: Volume Infused:
        PrsWdgPrompt - ID(634): NearViewVolumeInfusedUnitsPrompt - Text: mL
        PrsWdgPrompt - ID(633): NearViewVolumeInfusedPrompt - Text: 0.49
        PrsWdgPrompt - ID(618): NearViewTimeTitlePrompt - Text: Time Remaining:
        PrsWdgPrompt - ID(629): NearViewTimeUnitsPrompt - Text: hh:mm
        PrsWdgPrompt - ID(623): NearViewTimePrompt - Text: 01:00
        PrsWdgPrompt - ID(617): NearViewVtbiTitlePrompt - Text: VTBI:
        PrsWdgPrompt - ID(628): NearViewVtbiUnitsPrompt - Text: mL
        PrsWdgPrompt - ID(622): NearViewVtbiPrompt - Text: 99.6
        PrsWdgPrompt - ID(616): NearViewRateTitlePrompt - Text: Rate:
        PrsWdgPrompt - ID(627): NearViewRateUnitsPrompt - Text: mL/hr
        PrsWdgPrompt - ID(621): NearViewRatePrompt - Text: 100
        PrsWdgPrompt - ID(613): NearViewConcentrationPrompt - Text:
        PrsWdgPrompt - ID(612): NearViewInfusionPrompt - Text: Other Drug
        PrsWdgPrompt - ID(611): NearViewTitlePrompt - Text: A: STOPPED BASIC
      PrsCmnWindow ID(38): (BasicTherapyStoppedWindow) END DUMP
      PrsWdgKeypad ID(307): ChannelKeypad BEGIN DUMP
        PrsWdgButton - ID(1476): PiggybackButton - Status: ACTIVE Text: Piggyback
        PrsWdgButton - ID(1301): AdvancedButton - Status: INACTIVE Text: Advanced
        PrsWdgButton - ID(1483): ProgramButton - Status: ACTIVE Text: Basic
        PrsWdgButton - ID(1330): BolusButton - Status: ACTIVE Text: Bolus
      PrsWdgKeypad ID(307): ChannelKeypad END DUMP
    PrsCmnWindow ID(8): (TherapyWindow) END DUMP
    PrsWdgChannelTab - ID(1353): ChannelATabButton BEGIN DUMP
    Channel Identifier - Text: A
      PrsWdgButton - ID(1353): ChannelATabButton - Status: ACTIVE Text:
      State: No Dose/Amount or Rate Limits
      PrsWdgPrompt - ID(442): ChannelTabInfusionPrompt - Text: Other Drug
      PrsWdgInfusionIcon - ID(356): InfusionIconA - Text: Basic
    PrsWdgChannelTab - ID(1353): ChannelATabButton END DUMP TABLE 1-continued Infusion Pump User Interface State Embodiment

```
    PrsWdgChannelTab - ID(1356): ChannelBTabButton BEGIN DUMP
      Channel Identifier - Text: B
        PrsWdgButton - ID(1356): ChannelBTabButton - Status: ACTIVE Text:
        PrsWdgPrompt - ID(446): ChannelTabVolumeUnitsPrompt - Text: mL
        PrsWdgPrompt - ID(444): ChannelTabVolumePrompt - Text: 0
        PrsWdgPrompt - ID(445): ChannelTabRateUnitsPrompt - Text: mL/hr
        PrsWdgPrompt - ID(443): ChannelTabRatePrompt - Text: 0
    PrsWdgChannelTab - ID(1356): ChannelBTabButton END DUMP
    PrsWdgPatientInfoButton - ID(1473): PatientInfoButton BEGIN DUMP
        PrsWdgPatientInfoButton - ID(1473): PatientInfoButton - Status: ACTIVE
          CCA Text: Default
        Patient Id:
    PrsWdgPatientInfoButton - ID(1473): PatientInfoButton END DUMP
    PrsWdgButton - ID(1403): FarviewButton - Status: SELECTED Text:
  PrsCmnWindow ID(7): (AchannelWindow) END DUMP
  PrsWdgKeypad ID(308): DeviceKeypad BEGIN DUMP
    PrsWdgDeviceButton - ID(1312): AlarmMinimizedButton - Status: INACTIVE Text: Alarm
    PrsWdgDeviceButton - ID(1523): StandbyButton - Status: ACTIVE Text: Standby
    PrsWdgDeviceButton - ID(1427): LockButton - Status: ACTIVE Text: Lock
    PrsWdgDeviceButton - ID(1438): LogsButton - Status: ACTIVE Text: Logs
    PrsWdgDeviceButton - ID(1510): SettingsButton - Status: ACTIVE Text: Settings
    PrsWdgDeviceButton - ID(1439): ModeButton - Status: ACTIVE Text: Mode
  PrsWdgKeypad ID(308): DeviceKeypad END DUMP
  PrsWdgStatusBar - ID(369): StatusBar BEGIN DUMP
    PrsWdgPrompt - ID(306): CurrentTime - Text: 10:42 AM
    PrsWdgBatteryIcon - ID(371): BatteryIcon STATE: BatteryOneQtrCharging
    PrsWdgWirelessIcon - ID(372): WirelessIcon STATE: WirelessSignalNoDevice
  PrsWdgStatusBar - ID(369): StatusBar END DUMP
PrsCmnWindow ID(2): (MainWindow) END DUMP
```

In one or more embodiments, the current infusion state of the infusion pump may be transmitted to the controller separately, or otherwise known to the controller or derived from the current infusion pump user interface state, for example as obtained from a message in human or computer readable format. In either case, the command to be executed is executed if the command to change the infusion state of the infusion pump is able to be successfully executed based on the command, the current infusion state of the infusion pump and the current infusion pump user interface state. For example, in one scenario, the command is not executed if there is no administration set or cassette hooked up to the infusion pump in order to infuse a desired infusion of insulin or other drug. In another scenario, the command is not executed if the infusion pump is currently shutdown for an alarm as shown in FIG. 4, or busy delivering another infusion or even another drug in a piggyback operation. Embodiments of the invention thus provide a level of robust sanity checking for infusion delivery that provides the highest level of safety possible.

While the invention herein disclosed has been described by means of specific embodiments and applications thereof, numerous modifications and variations could be made thereto by those skilled in the art without departing from the scope of the invention set forth in the claims.

What is claimed is:

1. An infusion pump automation system comprising:
an infusion pump comprising a display configured to display an infusion pump user interface;
a remote processor that is remote to the infusion pump comprising:
a controller interface configured to communicate with the infusion pump;
a communications interface configured to receive a command from a computing system over a network, the command configured to change a first infusion state of the infusion pump to a second infusion state; and
a controller coupled with the controller interface, wherein said controller is configured to:
receive the command generated from the computing system;
determine, from the infusion pump, the first infusion state;
retrieve user interface data from the displayed infusion pump user interface on the display;
parse infusion parameters from the retrieved user interface data;
determine a user interface state based on the parsed infusion parameters;
verify that the command can be executed by the infusion pump based on the first infusion state of the infusion pump and the user interface state;
transmit an instruction for executing the command to the infusion pump to change the infusion pump from the first infusion state to the second infusion state based on the verification;
confirm, from the infusion pump, the execution of the command; and
transmit an indication of the confirmation from the infusion pump to the computing system over the network.

2. The infusion pump automation system of claim 1, wherein said controller is further configured to associate the infusion pump with a medication, a dose and a patient.

3. The infusion pump automation system of claim 1, wherein said controller is further configured to translate the command into an infusion specific command based on a particular type of the infusion pump.

4. The infusion pump automation system of claim 1, wherein said command to change the infusion state of the infusion pump comprises a medication, a dose and a patient.

5. The infusion pump automation system of claim 1, wherein said infusion pump is configured to display said command on said infusion pump user interface.

6. The infusion pump automation system of claim 1, wherein said controller is further configured to accept receive a confirmation input button request from said infusion pump.

7. The infusion pump automation system of claim 1, wherein the instruction comprises a simulated button press command to said infusion pump to initiate infusion.

* * * * *